(12) United States Patent
Johansson

(10) Patent No.: US 9,687,565 B2
(45) Date of Patent: *Jun. 27, 2017

(54) DIAGNOSTIC KIT

(71) Applicant: RESPIRATORIUS AB, Lund (SE)

(72) Inventor: Martin Johansson, Limhamn (SE)

(73) Assignee: RESPIRATORIUS AB, Lund (SE)

( * ) Notice: Subject to any disclaimer, the term of this patent is extended or adjusted under 35 U.S.C. 154(b) by 27 days.

This patent is subject to a terminal disclaimer.

(21) Appl. No.: 14/972,127

(22) Filed: Dec. 17, 2015

(65) Prior Publication Data

US 2016/0101195 A1  Apr. 14, 2016

Related U.S. Application Data

(63) Continuation of application No. 14/367,520, filed as application No. PCT/SE2012/051421 on Dec. 18, 2012, now Pat. No. 9,295,738.

(60) Provisional application No. 61/579,113, filed on Dec. 22, 2011.

(30) Foreign Application Priority Data

Dec. 22, 2011 (SE) ...................... 1151249

(51) Int. Cl.
*A61K 49/00* (2006.01)
*A61K 51/04* (2006.01)
*C07D 471/04* (2006.01)
*C07B 59/00* (2006.01)

(52) U.S. Cl.
CPC .......... *A61K 49/00* (2013.01); *A61K 51/0455* (2013.01); *C07B 59/002* (2013.01); *C07D 471/04* (2013.01)

(58) Field of Classification Search
CPC ........ A61K 49/00; A61K 51/00; A61K 51/04; A61K 31/56
See application file for complete search history.

(56) References Cited

U.S. PATENT DOCUMENTS 7,344,702 B2 * 3/2008 Casebier ............ A61K 49/0002
424/1.11
8,226,929 B2  7/2012 Casebier et al.
2005/0191238 A1  9/2005 Casebier et al.
2008/0112884 A1  5/2008 Casebier et al.
2012/0276006 A1  11/2012 Casebier et al.

FOREIGN PATENT DOCUMENTS

| CN | 1925878 | 3/2007 |
|---|---|---|
| EP | 1669348 | 6/2006 |
| WO | 2005079391 | 9/2005 |
| WO | 2007021858 | 2/2007 |
| WO | 2010097410 | 9/2010 |

OTHER PUBLICATIONS

Extended European Search Report dated Aug. 10, 2015; Application No. 12858896.9.
International Search Report dated Apr. 4, 2013, corresponding to PCT/SE2012/051421.
Chinese Office Action dated May 24, 2016, in corresponding Chinese application 201280069796.5, English translation provided.
Pharmacokinetics Research and Evaluation on New Drug, edited by Minji Wei et al, Peking University Medical Press, pp. 354-370, 2008, published on Sep. 30, 2008.
Antonova, M.I. et al., "Bioorganicheskaya Chimiya," part VI, Tutorial M., MGMSU, 2010, 66 pages with English translation.
Russian Office Action issued Application No. 2014125849/15(042036), dated Jan. 13, 2017.
D.A. Harkevich, "Pharmakologiya," Moskva, Medicine, 1987, pp. 47-48 with English Translation of extracts.
K. Kubota et al., "FDG-PET for Lung Cancer," Bronchology: The Journal of the Japan Society for Bronchology, 2007, vol. 29, No. 3, pp. 164-169 with English Abstract.
English Translation of Russian Office Action issued in Application No. 2014125849/15(042036), dated Aug. 29, 2016.
English Translation of Japanese Office Action issued in Application No. 2014-548735, dated Sep. 13, 2016.

* cited by examiner

*Primary Examiner* — Michael G Hartley
*Assistant Examiner* — Jagadishwar Samala
(74) *Attorney, Agent, or Firm* — Young & Thompson

(57) ABSTRACT

Compounds and a method for imaging myocardial perfusion, including administering to a patient a compound linked to an imaging moiety, wherein the compound binds MC-1, and scanning the patient using diagnostic imaging. Kits including the compound or precursor compounds linked or not linked to an imaging moiety are also described.

3 Claims, 1 Drawing Sheet

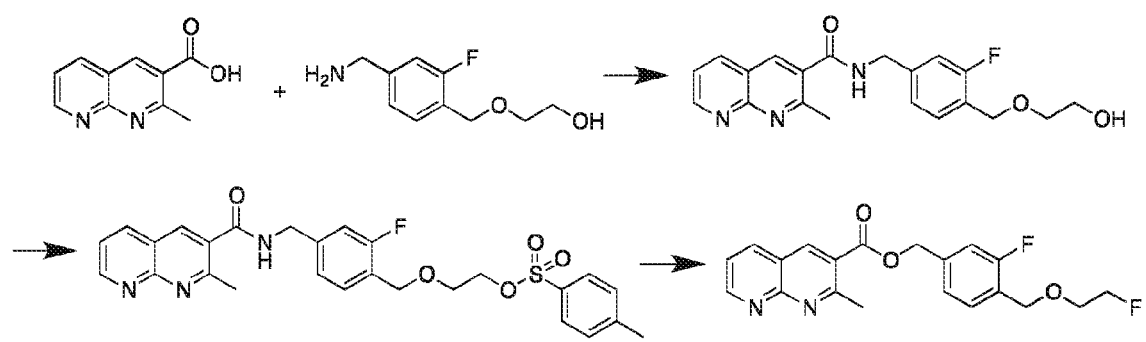

DIAGNOSTIC KIT

FIELD OF INVENTION

The present disclosure is directed to imaging agents, pharmaceutical compositions and methods for imaging myocardial perfusion, comprising administering to a patient a compound linked to an imaging moiety, wherein said compound binds MC-1, and scanning the patient using diagnostic imaging. The invention also relates to kits comprising said imaging agent or precursor compounds linked or not linked to an imaging moiety.

BACKGROUND OF INVENTION

Coronary artery disease (CAD) is a leading cause of death in the Western world. Imaging techniques for diagnosis and prognosis are very important for the treatment of CAD to reduce the mortality. Imaging for evaluation the myocardial blood flow to determine the treatment necessary (often surgery) is a critical part of CAD healthcare. Currently Single Photon Emission Computer Tomography (SPECT) is the mainstay of CAD imaging but improved diagnostic methods are needed.

Heart cells, myocardia, have a very high intracellular density, weight percentage, of mitochondria. It was therefore reasoned that compounds that selectively bind to mitochondria would be enriched in myocardia. Certain insecticides act through binding to the mitochondria complex I (MCI). Included in this group of insecticides are rotenone, pyridaben, tebufenpyrad and fenazaquin. It was believed that such compounds selective for MCI could be used for imaging mitochondrial rich tissue. A patent for the use of labelled rotenone for myocardial blood flow imaging was disclosed in 2001.

In 2005 BMS filed a patent (WO 2005/079391), describing $^{18}F$ labelled compounds based on the insecticides pyridaben, tebufenpyrad and fenazaquin for the use as PET-ligands for the diagnosis and imaging of mycocardial blood flow in CAD. The patents from BMS were later acquired by Lantheus Medical imaging. One of the compounds based on pyridaben, flurpiradaz (BMS747158), has been extensively studied and is now in phase III studies for myocardial imaging. Flurpiradaz has been found to provide superior assessment of myocardial function than the SPECT agent 99mTc sestamibi.

Respiratorius, a pharmaceutical company based in Lund, Sweden, has been working on discovering novel bronchodilating drugs. A central part of Respiratorius' discovery work is screening small molecules that can relax human airway tissue ex vivo. During this process a series of novel 1,8 naphthyridines were discovered as potent bronchorelaxing compounds (described in patent application WO/2010/097410). Upon further pharmacological studies it was found that members of this class of compounds bound to and inhibited mitochondrial complex I.

SUMMARY OF THE INVENTION

It has surprisingly been found that a bronchodilating compound belonging to a class of 1,8-naphthyridines also can inhibit mitochondrial function by relaxing the airway smooth muscle, alter mitochondrial function or bind to mitochondrial complex I. If the compounds are labelled with an imaging moiety a valuable diagnostic marker for myocardial perfusion imaging will be available.

The invention relates to an imaging agent having the structure

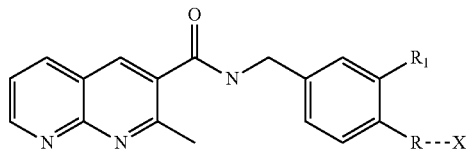

wherein $R_1$ is H, F, $CF_3$, Cl, R is a linker and X is an imaging moiety
or an analogue or pharmaceutically salt of said imaging agent.

In a second aspect the invention relates to a pharmaceutical composition comprising the imaging agent shown above and a pharmaceutically acceptable carrier, diluent, buffer. The imaging agent and composition gives rise to a high cardiac uptake to non-target ratio with minimal redistribution. It will also result in better image quality and disease detection and diagnosis. An almost linear myocardial uptake versus flow: up to 5 mL/min/g (high first-pass extraction) will be obtained. It allows quantification of absolute myocardial flow and will be effective with both exercise and pharmacologic stress. It will have an appropriate safety profile and be available as unit dose (such as 18F-labeled compound).

In a third aspect the invention relates to a method of imaging a heart in a patient comprising: administering to the patient a diagnostically effective amount of the imaging agent or pharmaceutical composition defined above, and obtaining an image of the heart of the patient. In a final aspect the invention relates to a diagnostic kit comprising a compound having the following formula

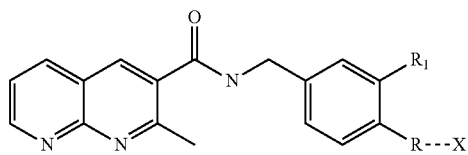

wherein $R_1$ is H, F, $CF_3$, Cl, R is a linker and X is a leaving group selected from the group consisting of tosylate, mesylate, triflate, nonaflate and halogen or an analogue of said compound and wherein said kit can be used to prepare an imaging agent as defined above.

BRIEF DESCRIPTION OF THE DRAWINGS

The FIGURE shows a synthetic pathway how to produce an imaging compound.

DETAILED DESCRIPTION OF THE INVENTION

Definitions

In the context of the present application and invention, the following definitions apply:

The term "Pharmaceutically acceptable salt" refers to those salts which retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

An analogue is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogues are often found using quantitative structure activity relationships (QSAR), with techniques such as those disclosed in Remington (The Science and Practice of Pharmacology, 19$^{th}$ Edition (1995), chapter 28).

The term "linking group," as used herein, refers to a portion of a molecule that serves as a spacer between two other portions of the molecule. Linking groups may also serve other functions as described herein. Examples of linking groups include linear, branched, or cyclic alkyl, aryl, ether, polyhydroxy, polyether, polyamine, heterocyclic, aromatic, hydrazide, peptide, peptoid, or other physiologically compatible covalent linkages or combinations thereof.

In a first embodiment the invention relates to an imaging agent having the structure

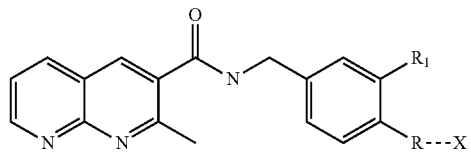

wherein $R_1$ is H, F, $CF_3$, Cl, R is a linker and X is an imaging moiety or an analogue or pharmaceutically acceptable salt of said imaging agent.

R may be a straight alkyl, ethyleneglycol (ether) or polyethylenglycol.

One example being

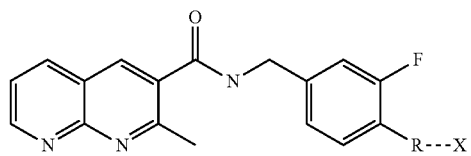

wherein R is a linker and X is an imaging moiety.

Another example being an imaging agent with the formula shown below:

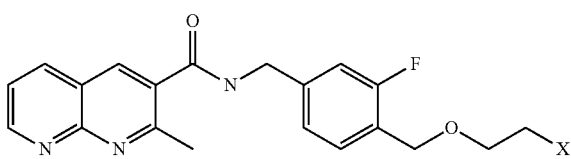

wherein X is an imaging moiety.

X may be a halogen isotope, such as a fluorine, bromine, chlorine or iodine isotope. Examples includes $^{18}$F, $^{19}$F, $^{120}$I, $^{121}$I, $^{122}$I, $^{123}$I, $^{124}$I, $^{125}$I, $^{127}$I, $^{131}$I, $^{35}$Cl, $^{37}$Cl, $^{75}$Br, $^{76}$Br, $^{77}$Br, $^{79}$Br, $^{80}$Br, $^{80m}$Br, $^{81}$Br or $^{64}$Cu. In a specific example $^{18}$F or $^{19}$F is used.

In another embodiment the invention relates to a pharmaceutical composition comprising the imaging agent as defined above and a pharmaceutically acceptable carrier, diluent, or buffer.

"Pharmaceutically acceptable" means a non-toxic material that does not decrease the effectiveness of the biological activity of the active ingredients, i.e., the peptide(s), polypeptide(s) or variants thereof. Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

The term "buffer" is intended to mean an aqueous solution containing an acid-base mixture with the purpose of stabilising pH.

The term "diluent" is intended to mean an aqueous or non-aqueous solution with the purpose of diluting the peptide in the pharmaceutical preparation. The diluent may be one or more of saline, water, human serum albumin, e.g., tris (hydroxymethyl) aminomethane (and its salts), phosphate, citrate, bicarbonate, alcohols including ethanol, sterile water, physiological saline, or balanced ionic solutions containing chloride and or bicarbonate salts or normal blood plasma cations such as calcium, potassium, sodium and magnesium. The labelled compound may be present in from 1.0 to 50 millicuries, such as 1.0-10, 10-20, 20-30, 30-40, 40-50 millicuries The pharmaceutical formulations according to the invention may be administered systemically. Routes of administration include parenteral (intravenous, subcutaneous, and intramuscular), oral, parenteral, vaginal and rectal. Suitable preparation forms are, for example dispersions, suspensions, aerosols, droples or injectable solution in ampule form and also preparations with protracted release of active compounds, in whose preparation excipients, diluents or carriers are customarily used as described above.

The imaging agents of the present invention may be used in methods of imaging, including methods of imaging in a patient. For example, the method may comprise administering the imaging agent to the patient by injection (e.g., intravenous injection), infusion, or any other known method, and imaging the heart of the subject wherein an event of interest is located.

The useful dosage to be administered and the particular mode of administration will vary depending upon such factors as age, weight, the diagnostic use contemplated, and the form of the formulation, for example, suspension, emulsion, microsphere, liposome, or the like, as will be readily apparent to those of ordinary skill in the art.

Typically, dosage is administered at lower levels and increased until the desirable diagnostic effect (e.g., production of an image) is achieved. In one embodiment, the above-described imaging agents may be administered by intravenous injection, usually in saline solution, at a dose of about 0.1 to about 100 mCi per 70 kg body weight (and all combinations and subcombinations of dosage ranges and specific dosages therein), or, in some embodiments, at a dose of about 0.5 to about 50 mCi. Imaging is performed using techniques well known to the ordinarily skilled artisan.

Another aspect of the present invention provides diagnostic kits for the preparation of imaging/diagnostic agents for determining (e.g., detecting), imaging, and/or monitoring at least a portion of the heart. Diagnostic kits of the present invention may comprise one or more vials containing a sterile, non-pyrogenic, formulation comprising a predetermined amount of a reagent (e.g., contrast agent precursor) of the present invention, and optionally other components such as chelating agents, solvents, buffers, neutrlization aids, lyophilization aids, stabilization aids, solubilization aids and bacteriostats, as described more fully below.

Some non-limiting examples of buffers useful in the preparation of contrast agents and kits include, for example, phosphate, citrate, sulfosalicylate, and acetate buffers. A more complete list can be found in the United States Pharmacopoeia.

Some non-limiting examples of lyophilization aids useful in the preparation of contrast agents and kits include, for example, mannitol, lactose, sorbitol, dextran, FICOLL.®. polymer, and polyvinylpyrrolidine (PVP).

Some non-limiting examples of stabilization aids useful in the preparation of contrast agents and kits include, for example, ethanol, ascorbic acid, ethanol, cysteine, monothioglycerol, sodium bisulfite, sodium metabisulfite, gentisic acid, and inositol.

Some non-limiting examples of solubilization aids useful in the preparation of contrast agents and kits include, for example, ethanol, glycerin, polyethylene glycol, propylene glycol, polyoxyethylene sorbitan monooleate, sorbitan monoloeate, polysorbates, poly(oxyethylene)-poly(oxypropylene)-poly(oxyethylene) block copolymers ("Pluronics.®.") and lecithin.

Some non-limiting examples of bacteriostats useful in the preparation of contrast agents and kits include, for example, benzyl alcohol, benzalkonium chloride, chlorobutanol, and methyl, propyl, or butyl paraben.

The compounds and compositions according to the invention may be used with imaging techniques such as positron emission tomography (PET) and Single Photon Emission Computed Tomography (SPECT). PET imaging is a diagnostic examination that involves the acquisition of physiologic images based on the detection of radiation from the emission of positrons from a radionuclide compound administered to the patient. The radionuclide compound is typically administered via intravenous injection. Different colours or degrees of brightness on a PET image represent different levels of tissue or organ function. SPECT imaging is a three-dimensional technique combined with computer assisted reconstruction of images of organs to reveal both anatomy and function. As with PET imaging, patients undergoing SPECT imaging is administered a radioactive tracer. PET and SPECT images may be used to evaluate a variety of diseases, and are commonly used in the fields of oncology, cardiology, and neurology.

Methods of Synthesizing Contrast Agents

Typically, imaging agents described herein may be synthesized by reacting at least a first component and a second component, such that a bond is formed there between. For example, 18F labeled compounds may be synthesized by reacting two components via displacement of an appropriate leaving group associated with at least one component. Examples of such leaving groups include sulfonic acid esters such as toluenesulfonate (tosylate, TsO-), methanesulfonate (mesylate, MsO-), or trifluoromethanesulfonate (triflate, TfO-), nonaflate or halogen. The leaving group may also be a halide, a phosphineoxide (via Mitsunobu reaction), or an internal leaving group (such as an epoxide or cyclic sulfate). Purification is generally performed via salt removal by reverse-phase chromatography.

Representative methods of making the compounds are described in the following examples. The foregoing chemical transformations may be conducted using techniques which would be readily apparent to one of ordinary skill in the art, in combination with the teachings described herein. In some cases, methods of synthesizing the contrast agents may include the use of one or more reaction solvents. Representative reaction solvents include, for example, DMF, NMP, DMSO, THF, ethyl acetate, dichloromethane, and chloroform. The reaction solution may be kept neutral or basic by the addition of an amine such as triethylamine or DIEA. In some cases, the chemical transformations (e.g., reactions) may be carried out at ambient temperatures and protected from oxygen and water with a nitrogen, argon or helium atmosphere.

In some embodiments, temporary protecting groups may be used to prevent other reactive functionality, such as amines, thiols, alcohols, phenols, and carboxylic acids, from participating or interfering in the reaction. Representative amine protecting groups include, for example, tert-butoxycarbonyl and trityl (removed under mild acidic conditions), Fmoc (removed by the use of secondary amines such as piperidine), and benzyloxycarbonyl (removed by strong acid or by catalytic hydrogenolysis). The trityl group may also used for the protection of thiols, phenols, and alcohols. In certain embodiments the carboxylic acid protecting groups include, for example, tert-butyl ester (removed by mild acid), benzyl ester (usually removed by catalytic hydrogenolysis), and alkyl esters such as methyl or ethyl (usually removed by mild base). All protecting groups may be removed at the conclusion of synthesis using the conditions described above for the individual protecting groups, and the final product may be purified by techniques which would be readily apparent to one of ordinary skill in the art, in combination with the teachings described herein.

Following examples are intended to illustrate, but not to limit, the invention in any manner, shape, or form, either explicitly or implicitly.

EXAMPLES

Example 1

Synthesis of an Imaging Compound

Example 1

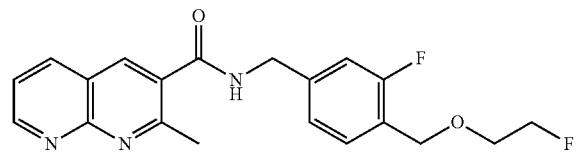 [SMILES: Cc1nc2ncccc2cc1C(=O)NCc1ccc(COCCF)c(F)c1]

N-[[3-fluoro-4-(2-fluoroethoxymethyl)phenyl]methyl]-2-methyl-1,8-naphthyridine-3-carboxamide A flask with a solution of 19 mg 2-[[2-fluoro-4-[[(2-methyl-1,8-naphthyridine-3-carbonyl)amino]methyl]phenyl]methoxy]ethyl 4-methylbenzenesulfonate (0.036 mmol), 26 mg Kryptofix 222 (4,7,13,16,21,24-Hexaoxa-1,10-diazabicyclo[8.8.8]-hexacosane) (0.069 mmol) and 4 mg KF (0.069 mmol) in 1.0 ml dry MeCN was added to a preheated oil bath and heated at 90 C for 30 min. The reaction mixture was cooled to room temperature and diluted with water. The mixture was extracted twice with EtOAc. The combined organic phases were washed with brine, dried (MgSO4) and concentrated. Flash chromatography gave 9.6 mg (72%).

$^1$H NMR (CDCl$_3$) δ 8.97 (dd, 1H), 8.03 (s,1H), 8.01 (m, 1H), 7.42 (m, 2H), 7.19 (dd, 1H), 7.13 (m, 1H), 7.08 (t, 1H), 4.67 (m, 2H), 4.65 (s, 3H), 4.53 (m, 1 H), 3.80 (m, 1 H), 3.73 (m, 1 H).

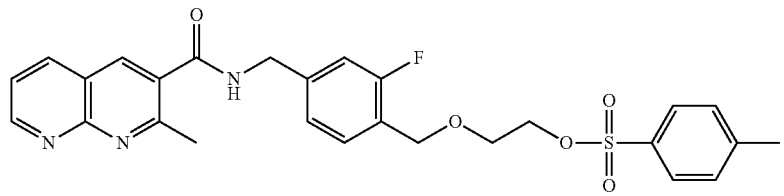 [SMILES: Cc1ccc(S(=O)(=O)OCCOCc2ccc(CNC(=O)c3cc4cccnc4nc3C)cc2F)cc1]

2-[[2-fluoro-4-[[(2-methyl-1,8-naphthyridine-3-carbonyl)amino]methyl]phenyl]methoxy]ethyl 4-methylbenzenesulfonate 25 mg tosylchloride (0.13 mmol) was added to a solution of 40 mg N-[[3-fluoro-4-(2-hydroxyethoxymethyl)phenyl]methyl]-2-methyl-1,8-naphthyridine-3-carboxamide (0.11 mmol), 23 µl diisopropylethylamine (6.13 mmol) and 13 mg DMAP (0.11 mmol) in 1.0 ml CH2Cl2 at room temperature. The solution was stirred for 2 h. The reaction mixture was placed directly on a SiO2 column and purified by flash chromatography (CH2Cl2/MeOH 50:1). Gave 52 mg (90%).

$^1$H NMR (CDCl$_3$) δ 8.89 (m, 1H), 7.99 (s, 1H), 7.82 (m, 1H), 7.73 (m, 3H), 7.31 (m, 4H), 7.13 (m, 2H), 4.65 (d, 2H), 4.51 (s, 2H), 4.15 (d, 2H), 3.68 (m, 2H), 2.77 (s, 3H), 2.41 (s, 3H)

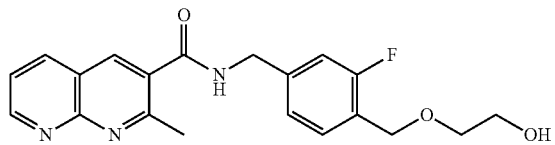 [SMILES: Cc1nc2ncccc2cc1C(=O)NCc1ccc(COCCO)c(F)c1]

N-[[3-fluoro-4-(2-hydroxyethoxymethyl)phenyl]methyl]-2-methyl-1,8-naphthyridine-3-carboxamide 45 µl oxalyl chloride (0.53 mmol) was added to a mixture of 50 mg 2-methyl-1,8-naphthyridine-3-carboxylic acid (0.27 mmol) in 3 ml CH2Cl2 with one drop DMF. The reaction mixture was stirred for 1.5 h and then evaporated to dryness under reduced pressure. The residue was dissolved in 3 ml CH2Cl2. 4 mg DMAP (0.03 mmol) and 188 µl triethyl amine (1.35 mmol) were added to the solution followed by 54 mg 2-[[4-(aminomethyl)-2-fluoro-phenyl]methoxy]ethanol (0.27 mmol). The reaction mixture was stirred for 4 h and then diluted with water. The phases were separated and the aqueous phase was extracted with CH2Cl2. The combined organic phases were dried (MgSO4) and concentrated. Flash chromatography (SiO2, CH2Cl2/MeOH 20:1) gave 36 mg (36%) of the title compound.

$^1$H NMR (CDCl$_3$) δ 8.82 (m, 1H), 7.96 (s, 1H), 7.95 (m, 1H), 7.88 (m, 1H), 7.31 (m, 2H), 7.10 (m, 2H), 4.60 (d, 2H), 4.56 (s, 2H), 3.75 (m, 2H), 3.61 (m, 2H), 2.68 (s, 3H)

The invention claimed is:
1. A kit comprising:
an imaging agent having the structure

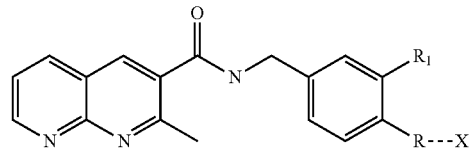

wherein R$_1$ is H, F, CF$_3$, Cl, R is a linker and X is an imaging moiety or radioactive isotope or an analogue or pharmaceutically acceptable salt of said imaging agent; and
an instruction how to use said kit.

2. A diagnostic kit comprising:
a compound having the following formula

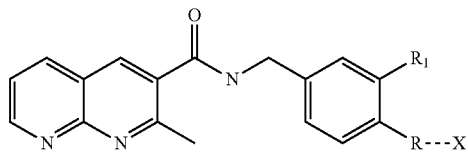

where R$_1$ is H, F, CF$_3$, Cl, R is a linker and X is a leaving group selected from the group consisting of tosylate, mesylate, triflate, nonaflate and halogen or an analogue of said;
wherein said kit can be used to prepare an imaging agent having the structure

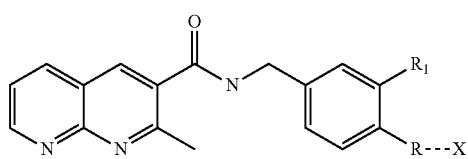

wherein R$_1$ is H, F, CF$_3$, Cl, R is a linker and X is an imaging moiety or radioactive isotope or an analogue or pharmaceutically acceptable salt of said imaging agent.

3. A kit comprising:
a pharmaceutical composition comprising:
an imaging agent having the structure

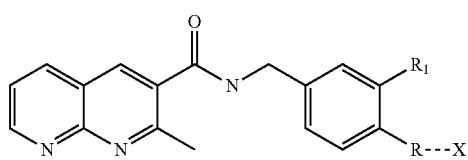

wherein R$_1$ is H, F, CF$_3$, Cl, R is a linker and X is an imaging moiety or radioactive isotope or an analogue or pharmaceutically acceptable salt of said imaging agent;
a pharmaceutically acceptable carrier, diluent, buffer; and
an instruction how to use said kit.

* * * * *